(12) United States Patent
Destrebecq et al.

(10) Patent No.: US 11,147,950 B2
(45) Date of Patent: Oct. 19, 2021

(54) ROBOTIZABLE MODULE FOR DRIVING AN ELONGATED FLEXIBLE MEDICAL MEMBER, MEDICAL ROBOT AND SYSTEM INCLUDING SUCH A MODULE

(71) Applicant: ROBOCATH, Rouen (FR)

(72) Inventors: Fabien Destrebecq, Bourgtheroulde (FR); Julien Maurel, Montjavoult (FR); Sébastien Deboeuf, Bonsecours (FR); Philippe Bencteux, Saint Martin du Vivier (FR)

(73) Assignee: ROBOCATH, Rouen (FR)

( * ) Notice: Subject to any disclaimer, the term of this patent is extended or adjusted under 35 U.S.C. 154(b) by 0 days.

(21) Appl. No.: 16/068,564

(22) PCT Filed: Jan. 5, 2017

(86) PCT No.: PCT/FR2017/050028
§ 371 (c)(1),
(2) Date: Jul. 6, 2018

(87) PCT Pub. No.: WO2017/118818
PCT Pub. Date: Jul. 13, 2017

(65) Prior Publication Data
US 2019/0038872 A1 Feb. 7, 2019

(30) Foreign Application Priority Data
Jan. 7, 2016 (FR) ...................................... 16 50105

(51) Int. Cl.
*A61B 34/20* (2016.01)
*A61M 25/01* (2006.01)
(Continued)

(52) U.S. Cl.
CPC ......... *A61M 25/0113* (2013.01); *A61B 34/20* (2016.02); *A61B 34/30* (2016.02); *A61B 2034/301* (2016.02); *A61B 2090/376* (2016.02)

(58) Field of Classification Search
CPC .... A61M 25/0113; A61B 34/30; A61B 34/20; A61B 2034/301; A61B 2090/376
(Continued)

(56) References Cited

U.S. PATENT DOCUMENTS

| | | | |
|---|---|---|---|
| 7,887,549 | B2 | 2/2011 | Wenderow et al. |
| 7,927,310 | B2 | 4/2011 | Bencteux |

(Continued)

FOREIGN PATENT DOCUMENTS

| | | |
|---|---|---|
| EP | 1792638 | 6/2007 |
| EP | 2777594 | 9/2014 |
| EP | 2821094 | 1/2015 |

OTHER PUBLICATIONS

International Search Report, PCTFR2017/050028, dated Mar. 15, 2017.
(Continued)

*Primary Examiner* — Kawing Chan
*Assistant Examiner* — Zemenay T Truneh
(74) *Attorney, Agent, or Firm* — Nixon & Vanderhye

(57) ABSTRACT

Disclosed is a module including: a base; a first drive member; and a second drive member. The second drive member is also mounted so as to be movable relative to the first drive member, in a degree of freedom other than rotational about the second axis, between a first and a second configuration. A motion transmission system transmits the driving movement generated by the drive motor to the second drive member in order to rotate the second drive member about the second axis between the first and second configurations.

16 Claims, 10 Drawing Sheets

(51) Int. Cl.
*A61B 34/30* (2016.01)
*A61B 90/00* (2016.01)

(58) Field of Classification Search
USPC .......................... 318/560; 606/130; 623/1.11
See application file for complete search history.

(56) References Cited

U.S. PATENT DOCUMENTS

| | | |
|---|---|---|
| D674,484 S | 1/2013 | Murphy et al. |
| D680,645 S | 4/2013 | Murphy et al. |
| D685,468 S | 7/2013 | Murphy et al. |
| 8,480,618 B2 | 7/2013 | Wenderow et al. |
| 8,828,021 B2 | 9/2014 | Wenderow et al. |
| 9,095,681 B2 | 8/2015 | Wenderow et al. |
| 9,168,356 B2 | 10/2015 | Wenderow et al. |
| 9,402,977 B2 | 8/2016 | Wenderow et al. |
| 9,623,209 B2 | 4/2017 | Wenderow et al. |
| RE46,442 E | 6/2017 | Bencteux |
| 2002/0177789 A1† | 11/2002 | Ferry |
| 2007/0123070 A1 | 5/2007 | Bencteux |
| 2010/0069833 A1 | 3/2010 | Wenderow et al. |
| 2010/0076308 A1 | 3/2010 | Wenderow et al. |
| 2010/0076309 A1 | 3/2010 | Wenderow et al. |
| 2010/0076310 A1 | 3/2010 | Wenderow et al. |
| 2010/0130987 A1 | 5/2010 | Wenderow et al. |
| 2010/0170519 A1* | 7/2010 | Romo .................... A61B 34/30 128/852 |
| 2012/0035596 A1* | 2/2012 | Tegg .................. A61M 25/0113 606/1 |
| 2012/0179167 A1 | 7/2012 | Wenderow et al. |
| 2013/0035537 A1* | 2/2013 | Wallace ................ A61B 34/30 600/8 |
| 2014/0058322 A1 | 2/2014 | Wenderow et al. |
| 2014/0276936 A1 | 9/2014 | Kokish et al. |
| 2014/0277333 A1* | 9/2014 | Lewis ................... A61B 34/30 623/1.11 |
| 2016/0158494 A1 | 6/2016 | Wenderow et al. |
| 2017/0065363 A1† | 3/2017 | Schuh |
| 2017/0071684 A1 | 3/2017 | Kokish et al. |
| 2017/0274181 A1 | 9/2017 | Wenderow et al. |

OTHER PUBLICATIONS

Feb. 7, 2020 letter from Braden M. Katterheinrich re: "Information regarding remarks submitted for U.S. Appl. No. 16/068,564".
U.S. Appl. No. 62/162,239, filed Sep. 9, 2015, 32 pages.†

\* cited by examiner
† cited by third party

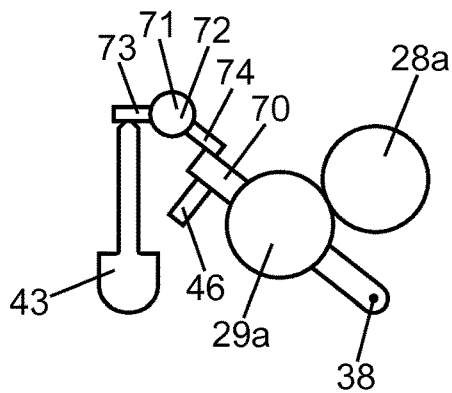
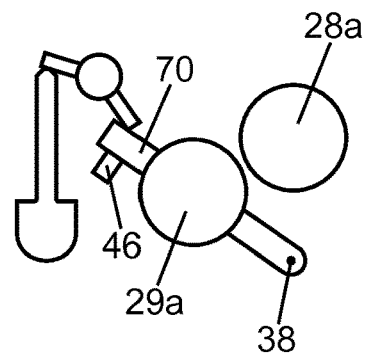
FIG. 11a  FIG. 11b
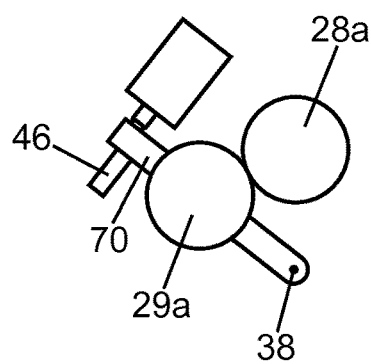
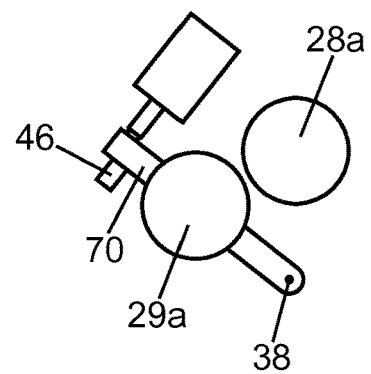
FIG. 12a  FIG. 12b
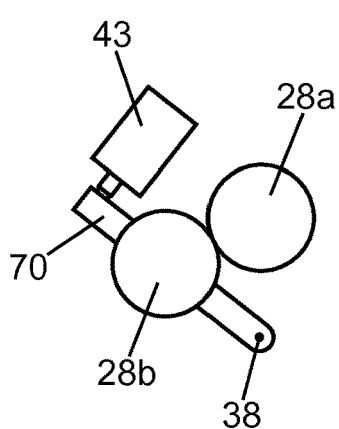
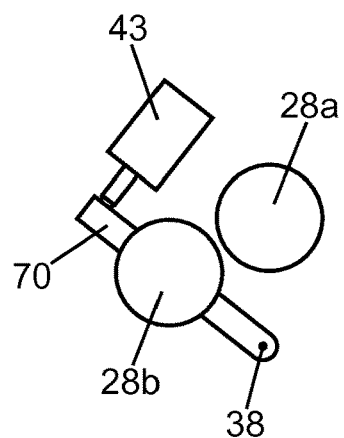
FIG. 13a  FIG. 13b

ROBOTIZABLE MODULE FOR DRIVING AN ELONGATED FLEXIBLE MEDICAL MEMBER, MEDICAL ROBOT AND SYSTEM INCLUDING SUCH A MODULE

The present invention relates to robotizable modules for driving an elongated flexible medical member.

Manual insertion of a catheter or guide in a patient is a relatively conventional surgical procedure. However, as this procedure is monitored by X-ray, the surgeon responsible for the procedure is exposed to substantial radiation if performing such an operation on many patients.

To reduce the risks for the surgeon, it is desirable to robotize such insertion. Such robotization is complex, because it is difficult to grip the catheter. The catheter is slippery, and must remain sterile. The reliability of these robotic systems despite these difficulties is a determining factor in their acceptance by the medical community.

Recently, a drive system was proposed in U.S. Pat. No. 7,927,310 which manages both the translation and rotation of the catheter. The catheter is held on a plate which rotates relative to a base in order to drive the rotation. The plate itself comprises a translational drive mechanism. In addition, use is made of remote motors remaining on the frame, and systems for transferring movement to the catheter. Indeed, not having embedded motors is preferred for reasons of power routing, footprint, and sterility.

Although this configuration is fully satisfactory, there is still a desire to further facilitate its use by medical staff. Deciding factors are fast startup and shutdown. Rapid, simple, and instinctive startup allows staff to avoid improper placement of the catheter in the robot and the subsequent issues. Fast shutdown may be necessary for manual intervention by medical staff during the procedure if such is needed.

More particularly, the invention relates to a robotizable module for driving an elongated flexible medical member. The module comprises a base.

The module comprises a first drive member defining a first axis and comprising a first peripheral driving surface around the first axis, the first drive member being mounted so as to rotate relative to the base about the first axis, and comprising a member connecting to a drive motor adapted to rotate the first drive member about the first axis.

The module comprises a second drive member defining a second axis parallel to the first axis, and comprising a second peripheral driving surface around the second axis, the second drive member being mounted so as to rotate relative to the base about the second axis.

The second drive member is also mounted so as to be movable relative to the first drive member, in a degree of freedom other than rotational about the second axis, between:

a first configuration wherein the first and second peripheral driving surfaces face each other with a first spacing between them, and a second configuration wherein the first and second peripheral driving surfaces face each other with a second spacing between them that is greater than the first spacing.

The module comprises an actuation system operable by a user, adapted to move the second drive member from at least one among the first and second configurations to the other among the first and second configurations.

US 2012/179,167 describes a robotizable module having the above features.

According to the invention, the module comprises a motion transmission system for transmitting the driving movement generated by the drive motor to the second drive member in order to rotate the second drive member about the second axis at least in any configuration between the first and second configurations.

With these features, one can very simply either engage the catheter with the robotizable module or disengage it, while decreasing the risk of rendering the robot inoperative due to these engagement/disengagement maneuvers.

In preferred embodiments of the invention, one or more of the following arrangements may possibly be used:

the motion transmission system is operating in the free configuration;

the motion transmission system comprises:

a first gear that is coaxial with the first drive member and forms an input member of the motion transmission system, an intermediate gear having an intermediate gear axis parallel to and offset from the first axis, the intermediate gear meshing with the first gear at least in any configuration between the first and second configurations, a transmission between the intermediate gear and the second drive member, transmitting the rotational motion of the intermediate gear about the intermediate gear axis into said rotational motion of the second drive member about the second axis.

the module comprises an elastic system biasing the second drive member from its second configuration towards its first configuration, and the actuation system is operable to move the second drive member from the first configuration and to the second configuration while compressing said elastic system;

the elastic system biases the actuation system which is integral to the second drive member;

the module comprises a locking system adapted to alternatively lock the second drive member in its free configuration or to release it, the actuation system being adapted to control the locking system;

the actuation system is electrically operable by the user;

at least one drive member is also mounted so as to be movable relative to the base in a translational motion along its axis;

said at least one drive member is mounted so as to be movable relative to the base in a translational motion along its axis in a translational path, and the first drive member comprises a deformable skirt, rubbing on the base during rotation of the first drive member relative to the base, and defining a closed perimeter on the base along the entire translational path;

the robotizable module further comprises a cover secured to the base and together with the base defining a housing defining an interior space in which are arranged at least a portion of the first drive member, at least a portion of the second drive member, and at least a portion of the actuation system, and wherein an actuation portion of the actuation system, a portion of the first drive member, and a portion of the second drive member extend out of the housing.

According to another aspect, the invention relates to a medical robot kit comprising a permanent portion and a removable portion, the permanent portion comprising a motor and a first coupling, the removable portion comprising such a robotizabie module provided with a second coupling complementary to the first coupling, the first and second couplings comprising at least one cam surface adapted to rotate the first and second couplings relative to each other with respect to a direction of assembly, during assembly of the removable portion to the permanent portion along the direction of assembly.

In a preferred embodiment of the invention, the following arrangement may possibly be used: the first coupling comprises a plurality of protrusions of concave shape, and the second coupling comprises a plurality of complementary recesses of complementary shape.

In a preferred embodiment of the invention, the first coupling comprises a centering cone, a protrusion that is movable relative to the centering cone in a sliding direction, and a biasing member biasing the protrusion relative to the centering cone during assembly of the removable portion to the permanent portion.

According to another aspect, the invention relates to a medical system comprising a hollow elongated flexible medical member extending along an axis of elongation, and such a medical robot or such a robotizable module, the hollow elongated flexible medical member being held between the first and second peripheral driving surfaces in the first configuration, the first drive member being rotatable relative to the base about the first axis in order to generate translational motion of the elongated flexible medical member along its axis of elongation.

In a preferred embodiment of the invention, it is possible to make use of the following arrangement: the first drive member is driven in translation relative to the base along the first axis in order to generate rotation of the elongated flexible medical member about its axis of elongation.

Other features and advantages of the invention will be apparent from the following description of one of its embodiments, given by way of non-limiting example and with reference to the accompanying drawings.

BRIEF DESCRIPTION OF THE DRAWINGS

In the drawings:

FIG. 1b is a top view of part of FIG. 1a,

FIGS. 11a and 11b are schematic views of the drive module according to one embodiment in two different configurations, FIGS. 12a, 12b and 13a, 13b are views corresponding to FIGS. 11a, 11b, for other embodiments.

In the different figures, the same references designate identical or similar elements.

DETAILED DESCRIPTION OF THE PREFERRED EMBODIMENTS

Figure 1A:
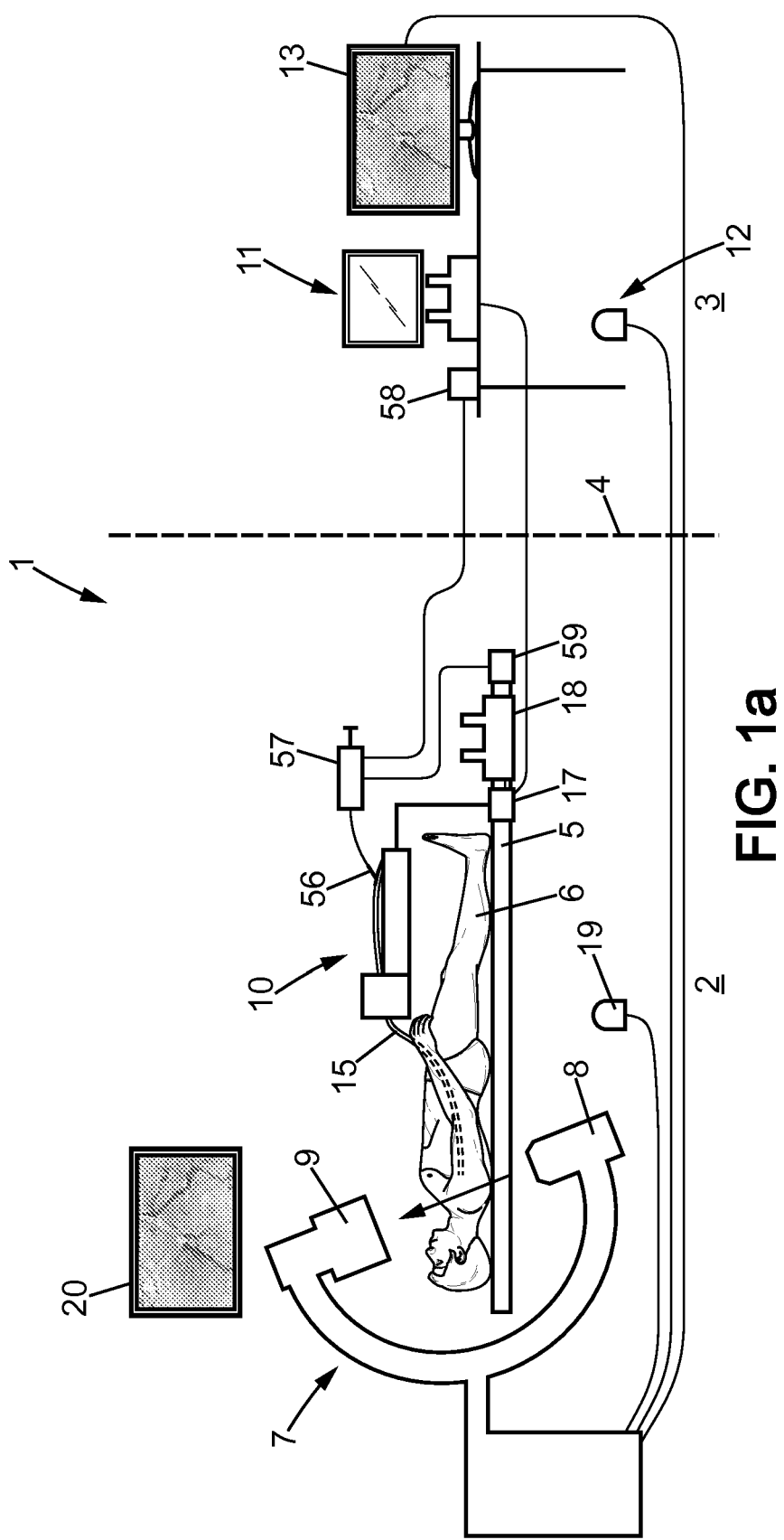
FIG. 1a is a schematic side view of a robotic arteriography facility.
Figure 1B:
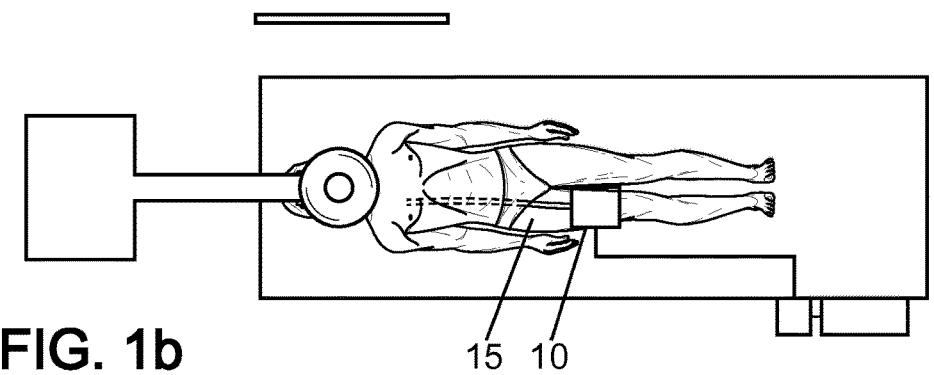

FIG. 1a schematically represents an arteriography facility 1. The arterography facility 1 is divided into two separate areas, an operating room 2 and a control room 3. The control room 3 may be close to the operating room 2 and separated from it by a simple radiopaque wall 4, for example a movable and/or removable screen, or remote. The equipment of the operating room 2 and control room 3 are functionally interconnected via a wired or wireless connection or network, etc.

The operating room 2 comprises an operating table 5 receiving a patient 6. The operating room 2 may also comprise a medical imager 7, in particular an X-ray imager, comprising a source 8 and a detector 9 arranged one on each side of the patient, possibly movable relative to the patient.

The arteriography facility 1 comprises a robot 10 located in the operating room 2.

The arteriography facility 1 comprises a control station 11 located in the control room 3. The control station 11 controls the robot 10 remotely. The arteriography facility 1 may also comprise, in the control room 3, one or more remote controls 12 for the imager 7, communicating with the imager 7 in order to control it remotely. The arteriography facility 1 may also comprise a display 13 located in the control room 3, communicating with the imager 7, for displaying in the control room 3 in real time the images captured by the imager 7.

The robot 10 can move an elongated flexible medical member 15 to be introduced into the body of a patient. The elongated flexible medical member 15 may be, for example, a member to be inserted into a canal of a patient and to be moved in said canal, particularly an artery or vein of a patient, through a desilet which provides an opening for access to the patient. The elongated flexible medical member may be a catheter. Alternatively, the elongated flexible medical member may be a catheter guide. A guide is generally of smaller transverse diameter than a catheter, which has a generally hollow portion near the patient or along its entire length so that the guide can move inside it, in particular inside the patient's body. The guide may also comprise a curved end, as will be described in more detail below.

The robot 10 can be controlled from the control station 11 to drive the elongated flexible medical member relative to the patient in at least one degree of freedom, as will be described in detail below. The robot may comprise a communication unit 17 for interfacing with the control station 11. If necessary, the robot 10 may comprise a local control unit 18, for controlling the robot from the operating room 2 when needed.

One will also note that all commands and feedback available in the control room 3 may also be available in the operating room 2 in order to carry out an operation locally, for example such as controls 19 for the imager and a screen 20 for displaying images captured by the imager 7.

The hollow elongated flexible medical member 15 may be connected to a connector 56 for injecting a contrast medium to facilitate imaging inside the patient. The arteriography facility may comprise a contrast medium injector 57 connected to the connector 56, controllable by controls 58 arranged in the control room 3. Controls 59 for the contrast medium injector may also be locally present in the operating room 2.

In the following, the reference 15 will alternatively be used to designate the guide 15", the catheter 15', or generally an elongated flexible medical member to be inserted into the body of a patient. For example, it may be a surgical catheter. Such a surgical catheter may be of smaller diameter than an outer catheter, so as to be guided inside the latter, coaxially within the patient, and may be hollow so as to be guided on the guide within the patient.

The connector 56 comprises a main branch 75 which the juxtaposed catheter 15' and guide 15" pass through. The distal end of the main branch 75 is assembled to an outer catheter (not shown) extending within the patient and within which the catheter 15' and guide 15" extend. The contrast medium is injected into the outer catheter by means of a secondary branch 76 of the connector 56.

Figure 2A:
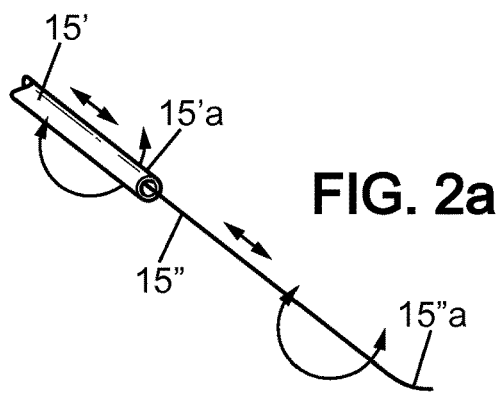
FIGS. 2a-2c are diagrams illustrating the modes of movement of the members to be driven.

FIG. 2a shows the various degrees of freedom possible with the present system. The guide 15" is shown with its front end 15"a slightly curved with respect to the main longitudinal axis of the guide, with an opening at the front end 15'a of the catheter 15'. The catheter 15' can be subjected to two distinct movements:

translation along its longitudinal axis,
rotation about its longitudinal axis.

These movements may be generated in one direction or the another.

Where appropriate, the catheter 15' may be subjected to a movement combining the two basic movements described above.

Where appropriate, the catheter 15' may be subjected to two movements combining the two basic movements described above, in different combinations.

The guide 15" can be subjected. to two distinct movements:

translation along its longitudinal axis,
rotation about its longitudinal axis.

These movements may be generated in one direction or in the other.

Where appropriate, the guide 15" may be subjected to a movement combining the two basic movements described above.

Where appropriate, the guide 15" may be subjected to two movements combining the two basic movements described above, in different combinations.

In some cases, the catheter itself is provided with a curved end, either to enable navigation according to the same principle as a guide, or to facilitate its positioning in an anatomical area having a particular curvature.

Figure 2B:
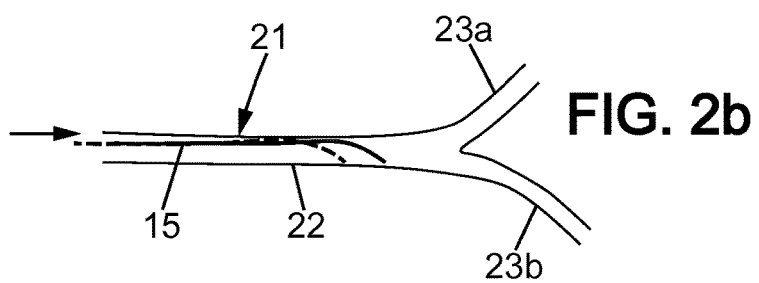
Figure 2C:
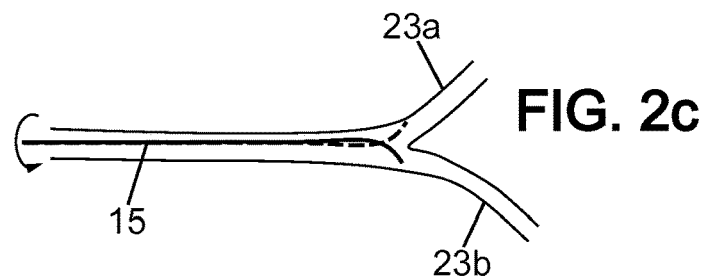

FIG. 2b depicts an artery 21 of a patient, comprising a main trunk 22 and two branches 23a, 23b leading to the main trunk. FIG. 2b illustrates the translational motion of an elongated flexible medical member 15 (here a guide 15") in translation between a retracted position represented by dotted lines and an advanced position represented by solid lines. In FIG. 2c, in the same artery, a rotation of the elongated flexible medical member 15 is represented, between a first position represented by dotted lines, where the elongated flexible medical member is ready for translational motion in the direction of branch 23a, and a second position represented by solid lines, where the elongated flexible medical member is ready for translational motion in the direction of branch 23b.

The assembly comprising the robot and the catheter and/or guide is called a "medical system".

Figure 3:
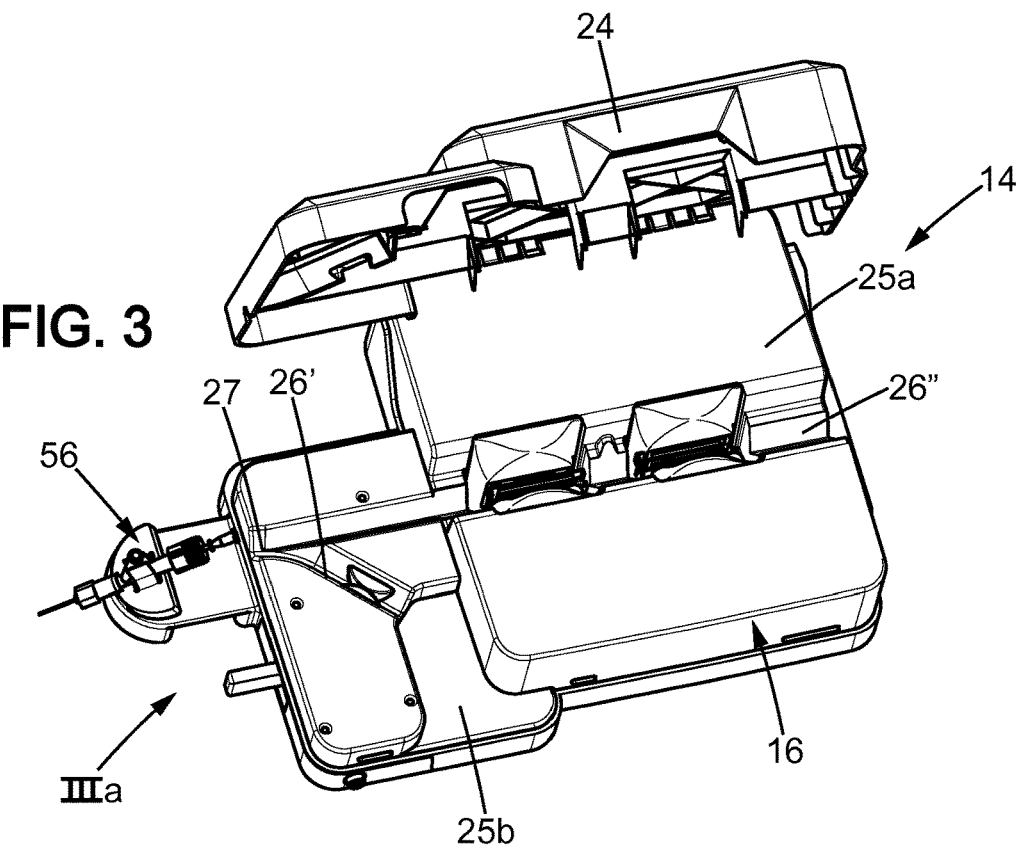
FIG. 3 is a perspective view of an exemplary embodiment of a robotizable module.

FIG. 3 shows a perspective view of a drive module 14. In this exemplary embodiment, the drive module 14 is disposable, and is provided for assembly in a sterile manner onto a motorized system. The drive module 14 comprises a housing 16 and a cover 24. The cover 24 is movable relative to the housing 16 between two respective configurations: open and closed. The configuration shown is the open configuration. In this configuration, the catheter 15' and the guide 15" are accessible. In the closed configuration, the catheter 15' and the guide 15" are not accessible at the module 14.

In the example shown, the drive module 14 drives the catheter 15' and the guide 15". However, this is illustrative, and the invention could be implemented in a system driving only the catheter 15' or only the guide 15".

In the present example, the drive module 14 comprises a first portion 25a driving the guide 15' and a second portion 25b driving the catheter 15". The first portion is substantially as described in QT FR2015/051566, incorporated by reference as if fully set forth herein for all purposes. It will be recalled that this system allows controlling the translation and/or rotation of the guide by a succession of repeated infinitesimal movements generated by a pair of actuating fingers. For various reasons (speed, security, reliability), two pairs of fingers can be used, for example as in the present embodiment, for example phase shifted.

The guide 15" lies in a channel 26". The catheter 15' lies in a channel 26'. The channels 26' and 26" meet at a common channel 27 which both the catheter 15' and the guide 15" lie within. Use is made for example of a "rapid exchange" catheter, meaning it has an opening providing access to the guide in its side wall. This access opening is located downstream of the common channel 27. This allows the guide 15" to run parallel to and outside the catheter 15' at least to the access opening, where the guide 15" passes inside the catheter to protrude from the distal end of the catheter into the patient's body as shown in FIG. 2a.

One will note that, in the illustration, the connector 56 is carried by a movable support 77, which is shown in a retracted configuration facilitating placement of the catheter 15' and guide 15' in their respective channels 26', 26". Following this placement, the support 77 is moved and folded so that the end 75a of the main branch is facing the common channel 27. This enables proper insertion of the catheter 15' and guide 15" through the connector 56.

The second portion 25b will be described in more detail below, particularly in relation to FIG. 3a.

Figure 3A:
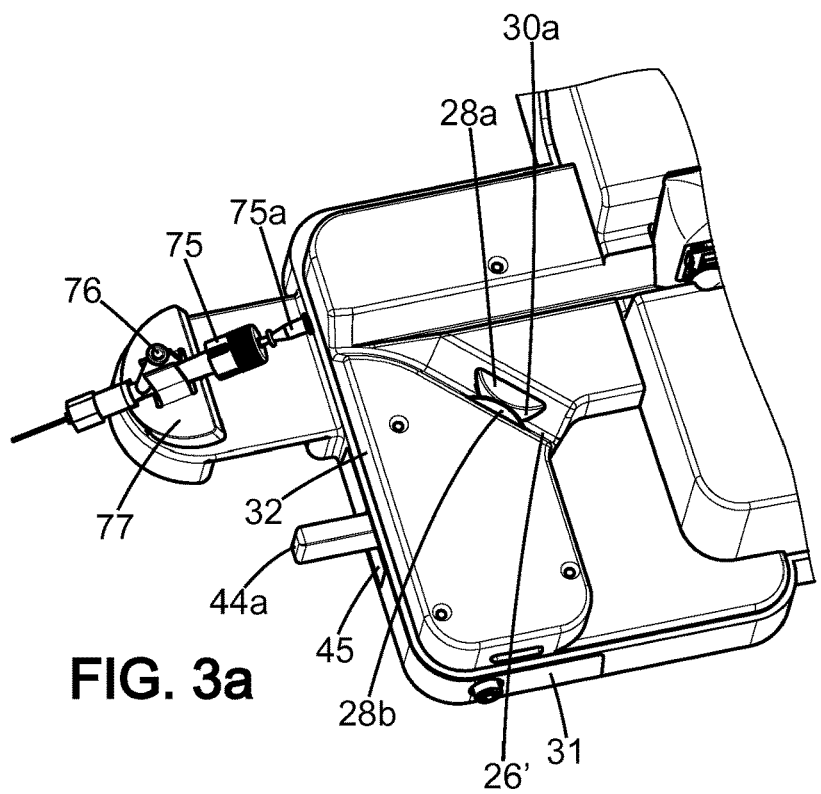
FIG. 3a is a perspective detailed view of the embodiment of FIG. 3.

As can be seen in particular in FIG. 3a, there is a first drive member 28a defining a first axis 29a and comprising a first peripheral driving surface 30a around the first axis 29a.

The first drive member 28a is mounted so as to rotate relative to the housing 16 about the first axis 29a (in this case vertical).

A second drive member 28b defines a second axis 29b, and comprises a second peripheral driving surface 30b around the second axis 29b.

The second drive member 28b is mounted so as to rotate relative to the housing 16 about the second axis 29b.

The second axis 29b is parallel to the first axis 29a. It is also spaced apart from the latter in the drive configuration, which is the configuration shown in FIG. 3a, such that a portion of the first peripheral driving surface 30a and a portion of the second peripheral driving surface 30b are facing one another, spaced apart by a gap of approximately the thickness of the catheter 15'. Thus, the portion of the first peripheral driving surface 30*a* and the portion of the second peripheral driving surface 30*b* in question project into the channel 26'.

The housing 16 comprises a base 31 and a cover 32 which are assembled together, as can be seen in FIG. 3*a*. The base 31 and the cover 32 assembled together define an interior volume 41 within which the mechanism is arranged. Only a portion of the drive members 28*a*, 28*b* projects from the interior volume to drive the catheter. Most of the mechanism is arranged within the interior volume, reducing the risk of accidental access to the mechanism.

The second drive member 28*b* is mounted so as to be movable relative to the first drive member 28*a* in a degree of freedom other than rotational about the second axis 29*b*, between:

a first configuration called the drive configuration (FIG. 4*a*), where the first and second peripheral driving surfaces 30*a*, 30*b* face each other with a first spacing between them, and a second configuration called the free configuration (FIG. 4*b*), where the first and second peripheral driving surfaces 30*a*, 30*b* face each other with a second spacing between them that is greater than the first spacing.

During this motion, the second drive member 28*b* can be in an infinite number of intermediate configurations between the first and second configuration. In addition, it is possible that the free configuration is not the ultimate configuration of the system in the direction of movement from the drive configuration to the free configuration, and further movement of the second drive member 28*b* along this direction and beyond this configuration is possible. Similarly, it is possible that the drive configuration is not the ultimate configuration of the system in the direction of movement from the free configuration to the drive configuration, and further movement of the second drive member 28*b* along this direction and beyond this configuration is possible. The drive configuration defined by a given clamping of a catheter 15' of given diameter.

The description below shows an example mechanism enabling the transition from one to the other of these configurations.

The first drive member 28*a* is fixed to a shaft 33*a*, having the drive axis 29*a* as its axis and driven by a motor 34. In this manner, actuation of the motor 34 generates rotation of the first drive member 28*a* about axis 29*a*. The shaft 33*a* thus establishes a connection between the motor 34 and the first drive member 28*a*.

The mechanism also comprises a motion transmission system 35 transmitting the drive movement generated by the drive motor 34 to the second drive member 28*b*. This involves rotating the second drive member 28*b* about the second axis 29*b* in the proper direction, which is in the direction opposite to the direction of rotation of the first drive member 28*a*, so that the two drive members 28*a* and 28*b* drive the catheter 15' in translation.

In the example presented, the motion transmission system 35 comprises a first gear 36*a* that is coaxial with the first drive member 28*a*. The first gear 36*a* forms an input member of the motion transmission system 35.

The motion transmission system 35 comprises an intermediate gear 37 having an intermediate gear axis 38 parallel to and offset from the first axis 29*a*. The intermediate gear 37 meshes with the first gear 36*a* in both the drive (FIG. 4*a*) and free (FIG. 4*b*) configurations.

The motion transmission system 35 comprises a transmission 39 between the intermediate gear 37 and the second drive member 28*b*, transmitting the rotational motion of the intermediate gear 37 about the axis 38 of the intermediate gear to the rotational motion of the second drive member 28*b* about the second axis 29*b*.

In the present example, the transmission 39 comprises a belt which is integral in rotation about axis 38 with the intermediate gear 37 and with the second drive member 28*b* about axis 29*b*.

Thus, the intermediate gear 37 is fixed to an intermediate shaft 40 whose axis is axis 38. The intermediate shaft 40 is integral with the belt.

The second drive member 28*b* is integral with a shaft 33*b* whose axis is the second axis 29*b*. Shaft 33*b* is integral with the belt.

Shaft 33*b* is supported by a bracket 42, which is mounted so as to rotate freely on both shaft 40 and the second shaft 33*b*.

Figure 4A:
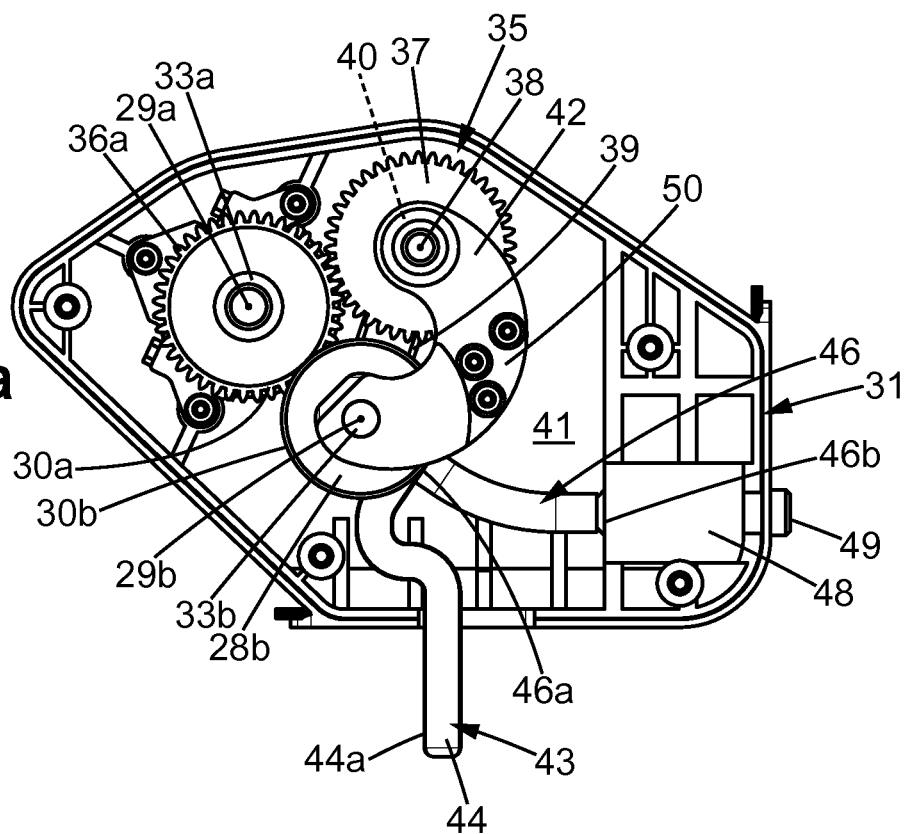
FIG. 4a is a top detailed view of FIG. 3 in a first configuration, the cover having been removed.
Figure 4B:
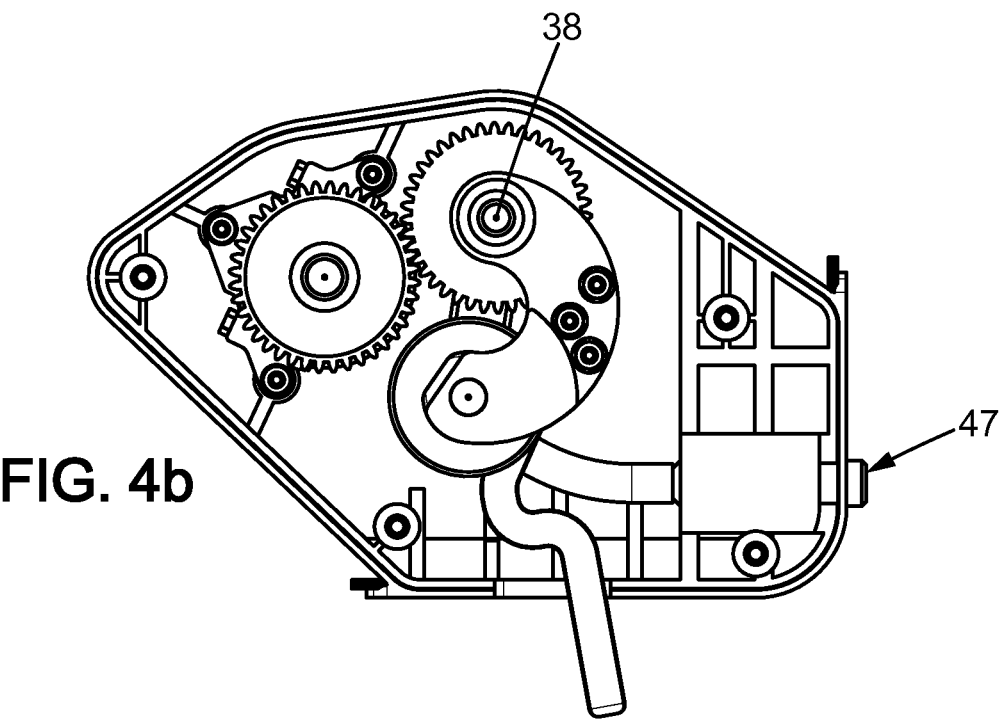
FIG. 4b is a view similar to FIG. 4a, in another configuration.
Figure 5:
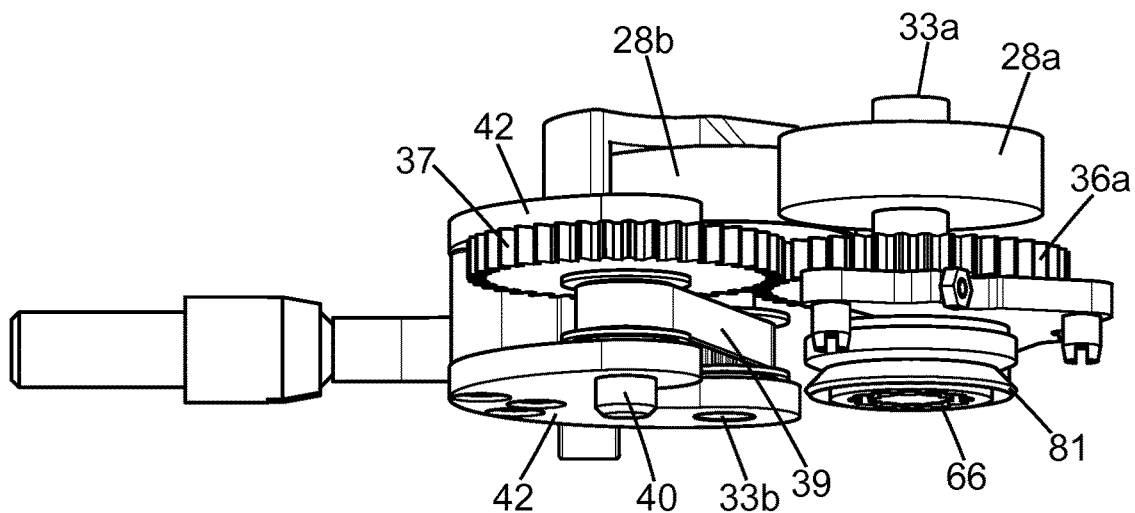
FIG. 5 is a side view of the mechanism of FIG. 4a, illustrated without the housing.

Thus, the second drive member 28*b* can move from its drive configuration, shown in FIG. 4*a*, to its free configuration, shown in FIG. 4*b*, by rotation about axis 38.

Note that in the free configuration of FIG. 4*b*, the motion transmission system 35 remains operational. In other words, the motor 34 rotates the second drive member 28*b* also in this configuration. This is not just true in the free configuration but in any intermediate configuration between the drive configuration and the free configuration, and even beyond. As the motion transmission system 35 is always operational, this ensures that when the second drive member 28*b* moves from its free configuration to its drive configuration, the catheter is driven by the two drive members without problems.

With these features, one can also ensure that catheters of different diameters are driven with the same mechanism, and/or that different clamping forces are applied to a given catheter (by bringing the two drive members 28*a*, 28*b* closer to one another).

Although the example above involves a particular motion transmission system 35, this is an illustrative example which is particularly compact; other variants are possible which achieve the same kinematics.

The degree of freedom when transitioning from the free drive configuration to the drive configuration is rotational about an axis parallel to the axes of the drive members. However, this an exemplary embodiment: other implementations appear possible.

The mechanism comprises an actuation system 43 operable by a user. The actuation system 43, when actuated, moves the second drive member 28*b* from its drive configuration to its free configuration.

The actuation system 43 comprises a lever 44 connected to the bracket 42, for example in an attachment region 50. The lever 44 comprises an actuating end 44*a* projecting beyond the housing 16 through an elongated slot 45 (FIG. 3*a*). The movement of the actuating end 44*a* of the lever 44 within the elongated slot 45 between a first and second position moves the second drive member 28*b* from its drive configuration to its free configuration.

If appropriate, an elastic system 46, such as a spring, biases the lever 44 towards its first position. In particular, this urges the second drive member 28*b* towards drive configuration.

Thus, when the second drive member 28*b* moves from its drive position to its free position due to user activation of the actuator 43, this compresses the elastic system 46.

The elastic system 46 comprises for example a spring, of which the first end 46*a* is fixed to the actuator 43 and the second end 46*b* to the base 31.

Furthermore, the position of the second end 46b relative to the base may be adjustable by an adjustment mechanism 47. This mechanism makes it possible to modify the clamping force of the drive members 28a, 28b on a given catheter 15', and/or to adapt to different catheter diameters.

The adjustment mechanism 47 comprises for example a nut 48 integral to the base 31, into which a screw 49 is screwed. The second end 46b of the spring bears against a stop surface of the screw 49. Screwing the screw 49 into the nut 48 changes the length of the space into which the spring can extend.

The housing is sealed by a seal 81 integral to the first drive member 28a, and rubbing on the base 31. This is a dynamic seal. The contact between seal 81 and base 31 surrounds an opening of the base 31 through which the housing 16 is coupled to the motorized stage 51.

Figure 6A:
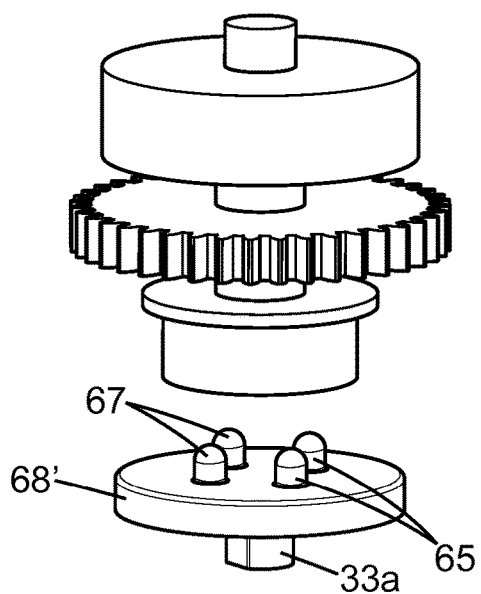
FIGS. 6a and 6b are two exploded views of the same coupling from different perspectives.
Figure 6B:
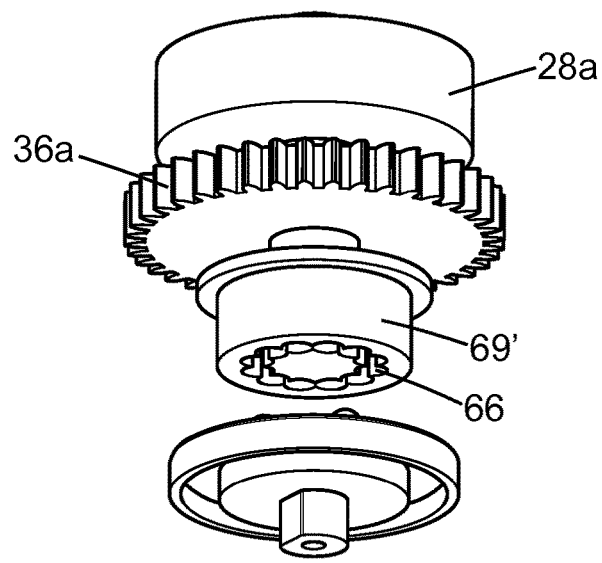

FIGS. 6a and 6b show an embodiment of a coupling between the motorized stage 51 and the housing 16 (the seal 81 is not shown in this figure). In this example, the shaft 33a driven by the motor comprises a coupling member 68' which has a plurality of identical pins 65 (in this case four). The pins 65 are distributed, for example uniformly distributed, in a circle passing through the axis 29a. The drive member 28a is integral with a coupling member 69' having a plurality of recesses 66 distributed along the circle passing through axis 29a. The recesses 66 are identical and are of complementary shape to the pins 65. The recesses 66 are tangent to each other to form a ring, so that regardless of the relative position of the pins 65 and recesses 66 around the axis 29a, the pins 65 are still all at least partially in front of a respective recess 66.

The pins 65 may have a domed end 67 to guide the act of coupling the recess on the shaft, if necessary with slight rotation of the drive member 28a about axis 29a by a distance at most equal to half a tooth.

FIG. 11a shows a variant embodiment of the actuation system described above in relation to FIGS. 4a and 4b. More specifically, FIG. 11a represents the module in the drive configuration, while FIG. 11b represents the free configuration. As one can see in these figures:

drive member 28a is fixed in the housing during its transition between the drive and free configurations, drive member 29a is mounted on a support 70 (like the bracket 50 for example), which is itself mounted so as to rotate within the housing about an intermediate axis 38 during its transition between the drive and free configurations.

The above description also applies to the alternative embodiment of FIGS. 12a and 12b and to the one of FIGS. 13a and 13b.

In FIG. 11a, a rocker 71 is used to transmit the movement of the actuator 43 to the drive member 29a. The rocker 71 is mounted so as to pivot about an axis 72, for example parallel to axis 38. The rocker 71 has a first arm 73 in contact with the actuator 43, and a second arm 74 in contact with the support 70.

The actuator 43 causes rotation of the rocker 71, the rocker's second arm 74 then pressing on the support 70 which causes rotation of the support 70 about its axis 38 (FIG. 11b).

This movement compresses a spring 46.

In a first variant, stopping the user actuation of the actuator 43 automatically returns the system to the drive configuration due to the release of the spring 46.

Alternatively, a system for locking the free configuration (FIG. 11b) may be provided. For example, a "push-pull" system may be implemented, similar to the insertion of cards into card readers. In the free configuration, user actuation of the actuator 43 unlocks the locking system, so that the system is returned to the drive configuration by the release of the spring 46.

In the above examples, mechanical actuation of the actuator via contact by a user may be provided. Such an embodiment ensures user actuation even during power failure.

Alternatively, as schematically represented in FIG. 12a, use may be made of an electrically controlled actuator. In this case, for safety reasons, FIG. 12b shows the system at rest (without electrical current applied). When current is applied, the actuator 43 rotates the support 70 about axis 38 relative to the rest position, thereby tensioning the spring 46. When power is cut off, for example to obtain a transition to the free configuration, the spring 46 pulls on the support 70 as shown in FIG. 12b. Also, in case of accidental power failure, the catheter can be disengaged from the mechanism.

Any type of linear actuator may be used. Fluid tightness at the controls is provided via an electrical connector.

As discussed above, either continuously operating release controls are provided, which in case of shutdown of the controls, automatically return the system to the drive configuration, or alternatively it may be arranged to lock the system in the free configuration.

One will also note that the actuator 43 may act directly on the support 70, rather than via a rocker.

Alternatively, as shown in FIGS. 13a, 13b, a spring 46 is not necessarily used. For example, the support 70 is connected directly to the actuator so that it follows the movements of the actuator.

Figure 7:
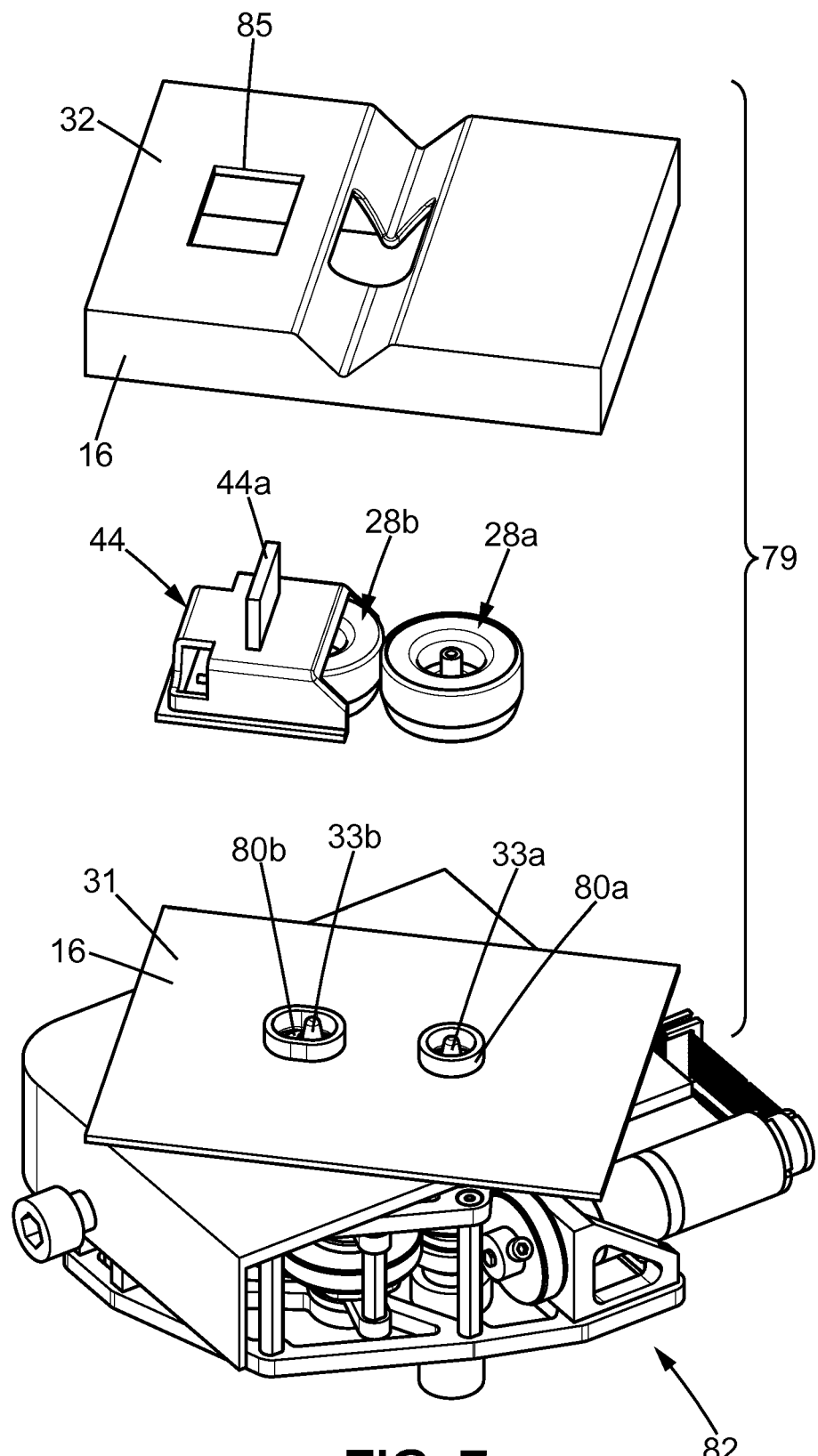
FIG. 7 is a perspective exploded view of a second embodiment.

FIG. 7 illustrates a second embodiment, below. The second embodiment differs from the first embodiment in certain features. A first difference is that the consumable part 79 which is disposable comprises the housing 16 (the cover 32 and the base 31) accommodating the drive members 28a and 28b, and the actuator 44.

The base 31 comprises a first opening 80a from which extends the first shaft 33a and a second opening 80b from which extends the second shaft 33b. The second opening 80b is large, to allow the second shaft 33b to travel relative to the base 31 (corresponding to the second drive member 29b transitioning between two configurations).

This embodiment requires a sterile connection between the first drive member 28a and the base 31, to reduce the risk of catheter contamination by the mechanism and/or jamming of the mechanism by substances conveyed by the catheter.

Figure 8:
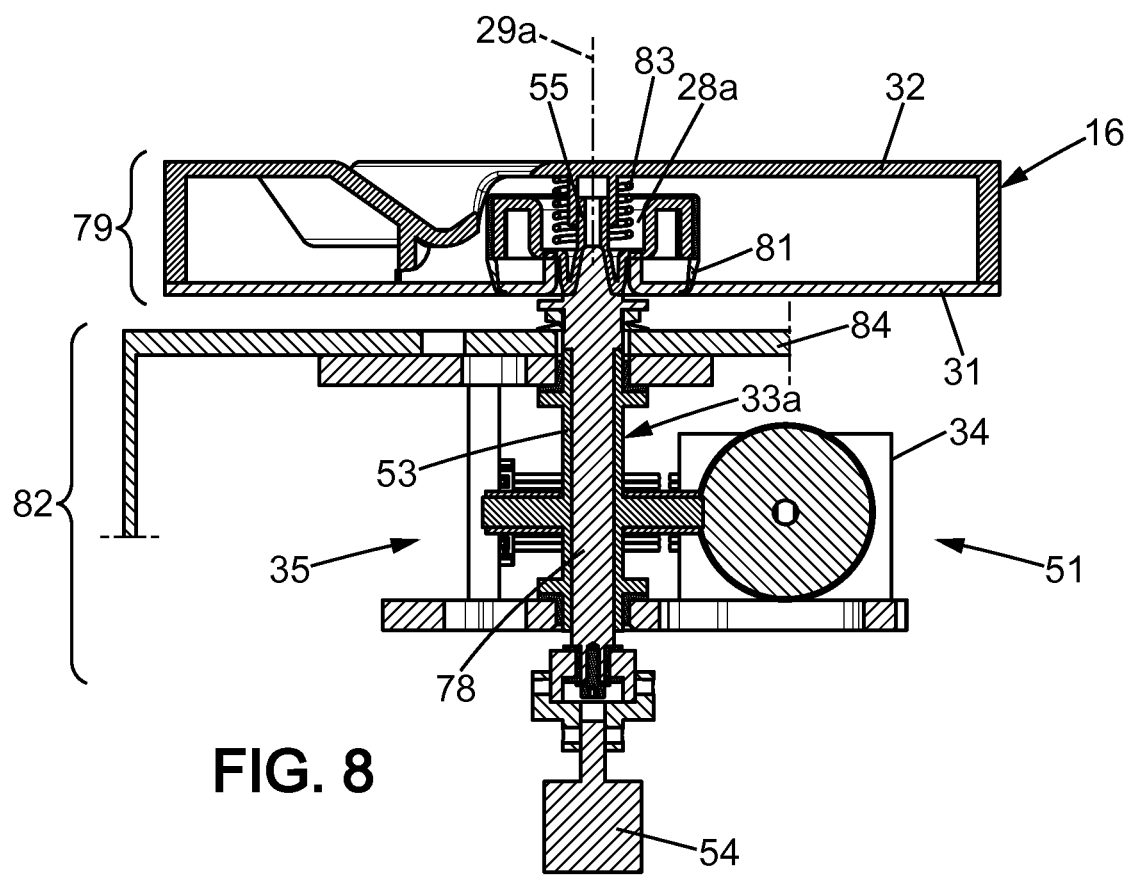
FIG. 8 is a vertical sectional view of the coupling of the module to the motor.

According to one embodiment, and as can be seen in FIG. 8, the drive member 28a is integral with a deformable skirt 81, rubbing on the base 31 and defining a closed perimeter on the base 31.

FIG. 8 illustrates a vertical section view of the driving of the drive member 28a by the motor 34. The drive module 14 comprises the housing 16 and a motorized stage 51.

FIG. 8 thus shows a medical robot comprising a permanent portion 82 and a removable portion, the permanent portion 82 comprising a motor 34 and a first coupling 68, the consumable part 79, which is removable, being provided with a second coupling 69 complementary to the first coupling 68.

It will be understood that where appropriate, the medical robot shown assembled in FIG. 8 may be provided in a kit, with the permanent portion and the removable portion to be assembled thereto. The removable portion, implemented as disposable, may be available in large quantities.

The shaft 33a is engaged with the first drive member 28a by a coupling that will be presented in detail below.

In the current case, also illustrated in FIG. 8 is an embodiment where the module rotates the catheter 15' about its axis of elongation. This rotation is achieved by a translational motion of the drive member 28a along its axis 29a. In this case, as the catheter 15' is clamped between the drive members 28a, 28b, displacement of one of the drive members relative to the other along this axis causes the catheter 15' to roll, thus rotating it about its axis of elongation.

In the current case, the rotation is limited to less than one turn relative to a starting position. It may be arranged that the neutral starting position is an intermediate position, thus allowing rotation of the catheter in one direction and in another, depending on the direction of translation of the drive member 28a.

In the example shown, the shaft 33a is implemented as two parts having complementary shapes which allow integral rotation of the two parts about axis 29a. The first portion is an inner core 78 integral to drive member 28a, and the second part is an outer casing 53 engaging with the motor 34. Furthermore, the inner core 78 is free to slide relative to the outer casing 53 along axis 29a. An actuator 54 controls the movement of the inner core 78 along axis 29a. An elastic means 83 such as a return spring returns the first drive member 28a to a rest position along axis 29a.

Controlling the actuator 54 moves drive member 28a along axis 29a via the inner core 78, the shaft 33a remaining in any position engaging with the motor 34.

Actuation of the motor 34 allows rotating drive member 28a as described above.

The skirt 81 is sufficiently long and deformable to ensure sterility at the interface between the drive member 28a and the base 31 along the entire path of drive member 28a along axis 29a.

As is understood from the above description, in this embodiment where the consumable part comprises a reduced number of components, the motion transmission system 35 is formed inside the housing 84 of the motorized stage 51.

Two exemplary embodiments for integrating gear 36a can be provided. According to a first variant, gear 36a is integral in translation with the shaft 33a. In this case, the intermediate gear 37 is of sufficient thickness to always mesh with gear 36a, regardless of its position along axis 29a. Alternatively, the shaft 33a is integral in rotation but free in translation relative to the gear 36a. To save space, the first variant can be implemented in the embodiment of FIGS. 4a and 4b, and the second variant can be implemented in the embodiment of FIG. 8.

Figure 9A:
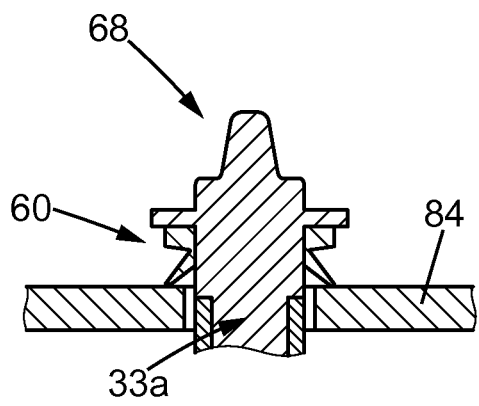
FIG. 9a is a sectional detailed view of FIG. 8, in a first configuration.
Figure 9B:
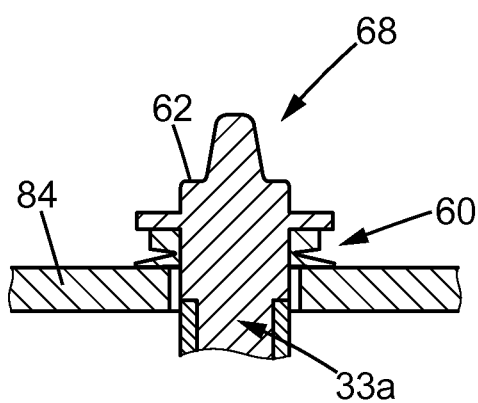
FIG. 9b is a view corresponding to FIG. 9a, in a second configuration.

FIGS. 9a and 9b show details of an embodiment concerning the sealing of the robot. Recall that this is a dynamic seal, with shaft 33a rotating to drive the catheter in translation.

Shaft 33a, and in particular the core 78, is integral with a seal 60. A sufficiently deformable seal 60 is chosen so that in the uppermost position, shown in FIG. 9a, it is rubbing against the housing 84, and in the lowermost position, shown in FIG. 9b, it is deformed so as to press against the housing 84. This embodiment is made possible by the small rotational travel of the catheter 15 (range of rotation less than +/−180°). Indeed, in the case of a rapid exchange catheter, it is desirable to avoid large rotational travel which can cause the guide to coil outside the catheter.

Figure 10A:
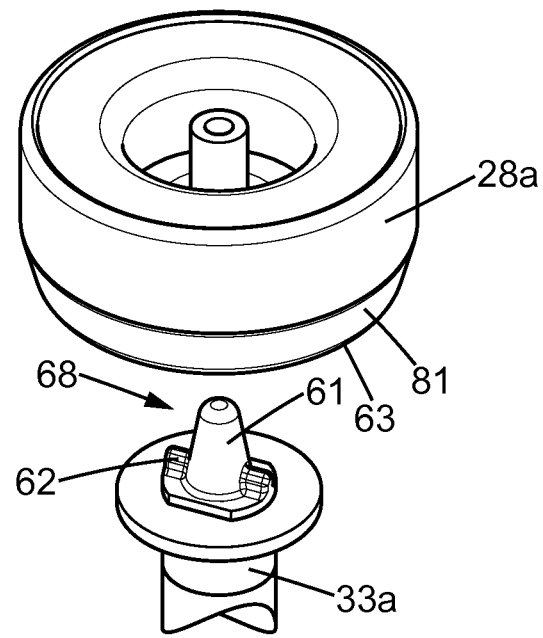
FIGS. 10a and 10b are exploded perspective views corresponding to FIGS. 6a, 6b, for a second example of a coupling.
Figure 10B:
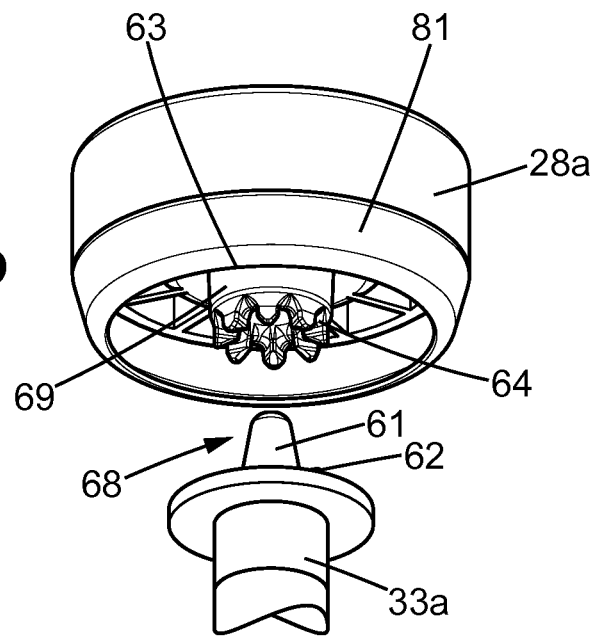

FIGS. 10a and 10b are perspective views of coupling the housing 16 on the motorized stage 51. For simplicity, the housing 16 is not represented in this figure.

As can be seen in FIG. 7, shaft 33a has a coupling member 68 provided with a centering cone 61 and one (or more) meshing teeth 62. The drive member 28a comprises a coupling member 69 that is complementary to coupling member 68. In particular, coupling member 69 comprises a cavity 63 complementary to the centering cone 61, and a plurality of drive teeth 64, for example distributed along the entire peripheral rim. During assembly of the housing 16 to the motorized stage 51 along a direction of assembly (substantially the direction of axis 29a), the centering cone 61 engages with the cavity 63 to guide the coupling, until tooth 62 engages with one of the teeth 64 of drive member 28a, if necessary with a slight rotation of drive member 28a by the cam about axis 29a by a distance at most equal to half a tooth.

As represented in FIG. 7, the actuation end 44a is not necessarily arranged at the housing 16, but may for example be in the upper surface. In this embodiment, the cover 32 comprises a window 85 in its upper surface, through which protrudes the actuating end 44a of the actuator 44 which is connected to the second drive member 28b. The actuator 44 comprises for example a contoured cover partially surrounding the second drive member 28b and connected thereto, so that they can both move towards the free configuration (shaft 33b is then moved within the opening 80b), while allowing rotation of the second drive member 28b about its axis.

Figure 14:
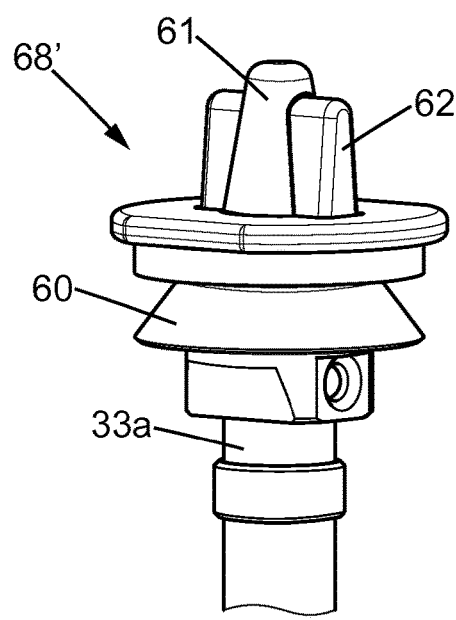
FIG. 14 is a perspective view of the portion mounted on the robot of a coupling according to a third example.
Figure 15:
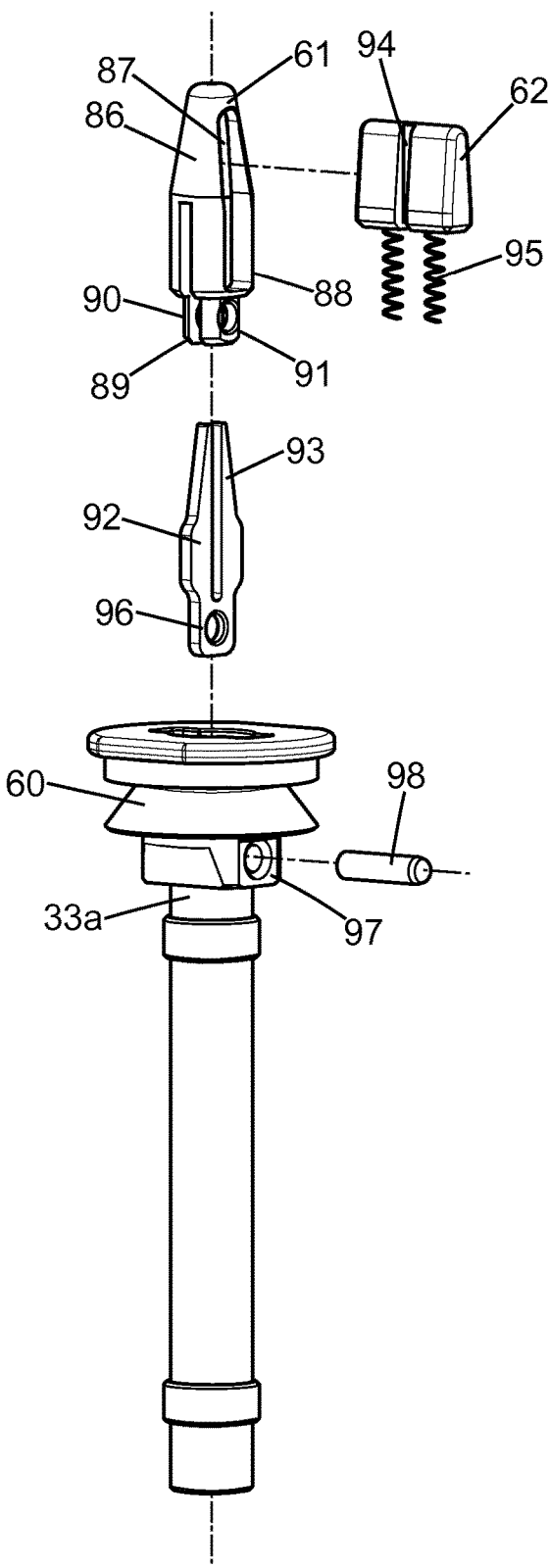
FIG. 15 is an exploded view of the device of FIG. 14.

According to another exemplary embodiment, a coupling may comprise a coupling member 68 on the robot side, as shown in FIG. 14, complementary to a coupling member on the consumable side (here again, not shown). The consumable-side coupling member is for example a coupling member 69 as illustrated above with reference to FIG. 10b. According to one feature of coupling member 68, the centering cone 61 and the tooth 62 are movable relative to each other. In particular, they are mounted in translation relative to one another, in particular along the direction of assembly of the consumable portion onto the robot.

For this, one can for example have the centering cone 61 include an outer casing 86 comprising a tapered end providing the centering function of the centering cone 61. The outer casing 86 also has an inner housing 87 accessible through a side opening 88 and a lower opening 89. The lower end 90 of the outer casing 86 also defines a bearing 91 for a transverse axis which will be described further below.

The centering cone 61 also comprises an inner core 92 which can be placed in the inner housing 87 from below through the lower opening 89. The inner core 92 has an elongated slot 93 along the direction of translation. This slot is open at the upper end of the inner core 92. The inner core 92 also comprises a bearing 96.

The tooth 62 has a form 94 complementary to the slot 93. It has for example a recess on the two opposite main faces of the tooth.

A biasing member 95 is mounted between the tooth 62 and the outer casing 86. This biases the tooth 62 upwardly along the direction of translation relative to the casing 86. For example, two springs are used as the biasing member. These two springs are then arranged one on each side of the form 94. The biasing member 95 is for example fixed to the tooth 62. For example, the tooth 62 has a bore in its lower face, for receiving an end portion of the spring.

The system just described is assembled as follows. The biasing member 95 is compressed, and the tooth 62 carrying them is inserted through the inner housing 87 via the side opening 88 until the form 94 is within the inner housing 87. The wings of the tooth then project from each side of the outer casing 86.

The biasing member 95 is released and presses against the outer casing 86 (on an inner face of the inner housing 87) and biases the tooth 62 upwards (position of FIG. 14).

The inner core 92 is mounted through the lower opening 89, the slot 93 engaging with the form 94. The bearings 91 and 96 are thus aligned.

The assembly is mounted on the base of the shaft 33a, the bearings 91 and 96 coming into alignment with a housing 97 thereof. A shaft 98 is inserted through the housing 97 and the bearings 91 and 96 to secure the coupling member 68 on the base of the shaft 33a.

In operation, the coupling member 68 is integral in rotational with the base of the shaft 33a, by means of shaft 98. During coupling, if the tooth 62 does not face a complementary recess of the complementary coupling member, but a protruding surface thereof, said protruding surface moves the tooth 62 downwards relative to the outer casing 86 by compressing the biasing member 95. During a subsequent rotation of the coupling member 68, when the tooth 62 then faces a complementary recess of the complementary coupling member, the biasing member 95 pushes the tooth 62 (position of FIG. 14) engaged therewith.

This embodiment allows using a highly crenellated geometry in the coupling members, which allows transmitting significant torque during use.

Thus, according to another aspect which is independent of the first, it seems that the invention relates to a robotizable module for driving an elongated flexible medical member, comprising:
a base 31,
a first drive member 28a defining a first axis 29a and comprising a first peripheral driving surface 30a around said first axis 29a, the first drive member 28a being mounted so as to rotate relative to the base 31 about the first axis 29a, and comprising a member 33a connecting to a drive motor 34 adapted to rotate the first drive member 28a about the first axis 29a,
wherein the first drive member 28a is also mounted so as to be movable relative to the base 31 in a translational motion along its axis 29a in a translational path,
wherein the first drive member 28a comprises a deformable skirt 81, rubbing on the base 31 during rotation of the first drive member relative to the base, and defining a closed perimeter on the base 31 along the entire translational path.

The invention claimed is:

1. A robotizable module for driving an elongated flexible medical member, comprising:
a base (31);
a drive motor (34);
a first drive member (28a), defining a first axis (29a) and comprising a first peripheral driving surface (30a) around said first axis (29a),
the first drive member (28a) being mounted so as to rotate relative to the base (31) about the first axis (29a) and comprising a member (33a) connecting to said drive motor (34) adapted to rotate the first drive member (28a) about the first axis (29a);
a second drive member (28b), defining a second axis (29b) parallel to the first axis (29a) and comprising a second peripheral driving surface (30b) around said second axis (29b),
the second drive member (28b) being mounted so as to rotate relative to the base (31) about the second axis (29b), and
the second drive member (28b) also being mounted so as to be movable relative to the first drive member (28a) between:
a first configuration wherein the first and second peripheral driving surfaces (30a, 30b) face each other with a first spacing therebetween, and
a second configuration wherein the first and second peripheral driving surfaces (30a, 30b) face each other with a second spacing therebetween that is greater than the first spacing;
an actuation system (43) operable by a user, adapted to move the second drive member (28b) from one of the first and second configurations to an other of the first and second configurations;
a motion transmission system (35) that transmits a driving movement generated by said drive motor (34) to the second drive member (28b) in order to rotate the second drive member (28b) about the second axis (29b) at least in any configuration between the first and second configurations,
said motion transmission system (35) comprised of
a first gear (36a) that is coaxial with the first drive member (28a) and forms an input member of the motion transmission system (35),
an intermediate gear (37) having an intermediate gear axis (38) parallel to and offset from the first axis (29a), teeth of the intermediate gear (37) entering into spaces formed by teeth of the first gear (36a) at least in any configuration between the first and second configurations, and
a transmission (39) between the intermediate gear (37) and the second drive member (28b), transmitting the rotational motion of the intermediate gear (37) about the intermediate gear axis (38) into said rotational motion of the second drive member (28b) about the second axis (29b); and
an elastic system (46) directly connected to the second drive member (28b) and biasing the second drive member (28b) from the second configuration towards the first configuration,
wherein the actuation system (43) is operable to move the second drive member (28b) from the first configuration and to the second configuration while compressing said elastic system (46).

2. The robotizable module according to claim 1, wherein the motion transmission system (35) operates in the second configuration.

3. The robotizable module according to claim 1, wherein the elastic system (46) biases the actuation system (43) which is integral with the second drive member (28b).

4. The robotizable module according to claim 1, further comprising:
a locking system adapted to alternatively lock the second drive member (28b) in the second free configuration or to release the second drive member (28b), the actuation system (43) being adapted to control the locking system.

5. The robotizable module according to claim 1, wherein the actuation system (43) is electrically operable by the user.

6. The robotizable module according to claim 1, wherein at least one drive member (28a) is also mounted so as to be movable relative to the base (31) in a translational motion along the first axis (29a).

7. The robotizable module according to claim 6, wherein said at least one drive member (28a) is mounted so as to be movable relative to the base (31) in a translational motion along the first axis (29a) in a translational path, and
wherein the first drive member (28a) comprises a deformable skirt (81), rubbing on the base (31) during rotation of the first drive member (28a) relative to the base (31), and defining a closed perimeter on the base (31) along the entire translational path.

8. The robotizable module according to claim 1, further comprising:
a cover (32) secured to the base (31) and together with the base defining a housing (16) defining an interior space (41) in which are arranged at least a portion of the first drive member (28a), at least a portion of the second drive member (28b), and at least a portion of the actuation system (43), wherein an actuation portion (44a) of the actuation system (43), a portion of the first drive member (28a), and a portion of the second drive member (28b) extend out of the housing (16).

9. A medical robot kit, comprising:
a permanent portion (51) and a removable portion,
the permanent portion comprising a motor (34) and a first coupling (68, 68'), and
the removable portion comprising a robotizable module according to claim 1, provided with a second coupling (69, 69') complementary to the first coupling (68, 68'),
wherein the first and second couplings (68, 68', 69, 69') comprise at least one cam surface adapted to rotate the first and second couplings (68, 68', 69, 69') relative to each other with respect to a direction of assembly, during assembly of the removable portion to the permanent portion (51) along the direction of assembly.

10. The medical robot kit according to claim 9, wherein the first coupling (68, 68') comprises a plurality of protrusions (65, 62) of concave shape, and the second coupling (69, 69') comprises a plurality of complementary recesses (66, 64) of complementary shape.

11. The medical robot kit according to claim 9, wherein the first coupling comprises a centering cone (61), a protrusion (62) that is movable relative to the centering cone (61) in a sliding direction, and a biasing member (95) biasing the protrusion (62) relative to the centering cone (61) during assembly of the removable portion to the permanent portion.

12. A medical system, comprising:
a hollow elongated flexible medical member extending along an axis of elongation; and
a medical robot according to claim 9,
the hollow elongated flexible medical member (15) being held between the first and second peripheral driving surfaces (30a, 30b) of the medical robot in the first configuration, the first drive member (28a) being rotatable relative to the base (31) about the first axis (29a) in order to generate translational motion of the elongated flexible medical member (15) along the axis of elongation.

13. The medical system according to claim 12, the first drive member (28a) being driven in translation relative to the base (31) along the first axis (29a) in order to generate rotation of the elongated flexible medical member (15) about the axis of elongation.

14. A medical system, comprising:
a hollow elongated flexible medical member extending along an axis of elongation; and
a robotizable module according to claim 1,
the hollow elongated flexible medical member (15) being held between the first and second peripheral driving surfaces (30a, 30b) in the first configuration of the medical robot, the first drive member (28a) being rotatable relative to the base (31) about the first axis (29a) in order to generate translational motion of the elongated flexible medical member (15) along the axis of elongation.

15. The medical system according to claim 14, the first drive member (28a) being driven in translation relative to the base (31) along the first axis (29a) in order to generate rotation of the elongated flexible medical member (15) about the axis of elongation.

16. The robotizable module according to claim 1, wherein the intermediate gear axis (38) is offset from the second axis (29b) of the second drive member (28b).

* * * * *